United States Patent [19]

Mitchell

[11] Patent Number: 4,874,900

[45] Date of Patent: Oct. 17, 1989

[54] PREPARATION OF PSEUDOIONONES

[75] Inventor: Peter W. D. Mitchell, Freehold, N.J.

[73] Assignee: Union Camp Corporation, Wayne, N.J.

[21] Appl. No.: 62,884

[22] Filed: Jun. 16, 1987

[51] Int. Cl.$^4$ .............................................. C07C 45/45
[52] U.S. Cl. .................................... 568/390; 568/345
[58] Field of Search ................................ 568/390, 345

[56] References Cited

U.S. PATENT DOCUMENTS 2,916,530 12/1959 Bloch .................................. 568/390
3,840,601 10/1974 Gradeff .............................. 568/390

FOREIGN PATENT DOCUMENTS 0062291 10/1982 European Pat. Off. ............ 568/390
546603 10/1974 U.S.S.R. ............................... 568/390
704938 12/1979 U.S.S.R. ............................... 568/390

Primary Examiner—James H. Reamer
Attorney, Agent, or Firm—Edward J. Sites

[57] ABSTRACT

A process is provided for the preparation of pseudoionones by the condensation reaction of citral with a ketone in the presence of lithium hydroxide catalyst.

15 Claims, No Drawings

PREPARATION OF PSEUDOIONONES

BACKGROUND OF THE INVENTION

1. Field of The Invention

The invention relates to an improved process for preparing ketones, and more particularly relates to an improved process for preparing pseudoionones by the condensation of citral and a ketone.

2. Brief Description of The Prior Art

The prior art is replete with descriptions of methods and procedures for preparing pseudoionones by the condensation of citral with a ketone. Exemplary of such descriptions are those pertaining to the condensation of citral with acetone to prepare pseudoionone.

Pseudoionone, also known as 6,10-dimethyl-3,5,9-undeca-trien-2-one, is an unsaturated ketone useful as an intermediate in the synthesis of vitamin A and odorants (such as ionone). A number of synthetic routes for its preparation have been developed. Some of these routes, which give a less pure product, are based on treatment of oil of lemon grass and acetone with bleaching powder, cobalt nitrate, and alcohol [Ziegler, J. Prakt. Chem. [2] 57, 493 (1898); Tiemann, Ber. 31, 2313 (1898); Haarman, Riemer & Co., German Patent No. 73,089].

The route which has been used in the prior art to make relatively pure product is based on condensation of citral with acetone in the presence of a condensation catalyst. The condensation catalysts which have been used have been solutions of bases in solvents, usually in water or alcohol. A number of these prior art processes are summarized in Organic Syntheses, Collective volume 3, 750 and utilize as bases aqueous barium hydroxide, a solution of sodium ethoxide in ethanol, metallic sodium (which is predissolved in alcohol according to the primary reference), and alcoholic sodium hydroxide. U.S. Pat. No. 3,480,677 to Meuly et al. (Nov. 25, 1969) cites the use of aqueous sodium hydroxide in the condensation of citral with acetone, and U.S. Pat. No. 3,840,601 to Gradeff (Oct. 8, 1974) cites the use of solutions of sodium hydroxide or sodium alkoxide in the condensation of citral with a ketone. The use of an aqueous sodium hydroxide solution as the catalyst for the citral-acetone condensation reaction has been commercially practiced. These prior art processes provide relatively impure crude products which must be purified by a painstaking and costly washing operation followed by a fractional distillation which must be done very carefully to remove close boiling by-products. Moreover, this requirement for distillation exposes the product to prolonged heating with formation of more by-products. The decomposition during distillation is aggravated by the presence of either the alkaline catalyst or any acid used to remove the alkaline catalyst. Moreover, the processes of the prior art generally have given satisfactory yields only with the use of a large excess of acetone, typically 10–20 moles per mole of citral, thus cutting down the space yield of the process and requiring a large and costly plant for a commercial scale of production.

The method of the present invention makes available a process for the preparation of pseudoionones with improved yields, at a rapid rate, and with simplified process operations. The product obtained is of a relatively high purity.

The method of the present invention also has a number of other important advantages. Namely, it simplifies a following distillation requirement since the crude product is of high assay with less foreshot and less high boiling residues to be removed. Lower quantities of isocitral aldols are produced as by-products with consequent fewer high boiling by-products to be separated. It also permits a simple filtration removal of the unused catalyst, allowing at least part of it to be recycled. Also, it allows the unused excess ketone to be recovered in a substantially anhydrous state (when the process is carried out under anhydrous conditions) facilitating recycle. The method of the invention is readily adaptable to continuous operation, using a packed column of catalyst, or a stirred vessel operated in continuous mode.

SUMMARY OF THE INVENTION

The invention comprises a method of preparing pseudoionones of the formula:

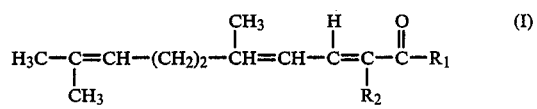

wherein $R_1$ represents hydrocarbyl of from 1 to 25 carbon atoms, inclusive; $R_2$ independently is selected from the group consisting of hydrogen and aliphatic hydrocarbyl of 1 to 10 carbon atoms, inclusive; and $R_1$ and $R_2$ when taken together with the two adjacent carbon atoms to which they are attached are members of an alicyclic ring, which comprises; the condensation of citral with a ketone of the formula:

wherein $R_1$ and $R_2$ have the meanings previously ascribed to them; in the presence of a catalytic proportion of lithium hydroxide.

The term "hydrocarbyl" as used herein means the monovalent moiety obtained upon removal of a hydrogen atom from a parent hydrocarbon. Representative of hydrocarbyl are alkyl of 1 to 25 carbon atoms, inclusive, such as methyl, ethyl, propyl, butyl, pentyl, hexyl, heptyl, octyl, nonyl, undecyl, decyl, dodecyl, octadecyl, nonodecyl, eicosyl, heneicosyl, docosyl, tricosyl, tetracosyl, pentacosyl and the isomeric forms thereof; aryl of 6 to 25 carbon atoms, inclusive, such as phenyl, tolyl, xylyl, napthyl, biphenyl, tetraphenyl and the like; aralkyl of 7 to 25 carbon atoms, inclusive, such as benzyl, phenethyl, phenpropyl, phenbutyl, phenhexyl, napthoctyl and the like; cycloalkyl of 3 to 8 carbon atoms, inclusive, such as cyclopropyl, cyclobutyl, cyclopentyl, cyclohexyl, cycloheptyl, cyclooctyl and the like; alkenyl of 2 to 25 carbon atoms, inclusive, such as vinyl, allyl, butenyl, pentenyl, hexenyl, octenyl, nonenyl, decenyl, undececyl, dodecenyl, tridecenyl, pentadecenyl, octadecenyl, pentacosynyl and isomeric forms thereof.

The method of the invention is particularly advantageous for preparing pseudoionone, methylpseudoionone, dimethylpseudoionone and ethylpseudoionone.

DETAILED DESCRIPTION OF THE PREFERRED EMBODIMENTS OF THE INVENTION

The method of the invention may be carried out by bringing the reactants together in stoichiometric proportions to effect condensation. Preferably a molar excess of the ketone of formula (II) is employed. Advantageously the mole ratio of ketone (II) to citral is from about 2:1 to 100:1; preferably 4:1 to 50:1.

Citral, also known as 3,7-dimethyl-2,6-octadienal is a constituent of oil of lemongrass and also present in oils of verbena, lemon, and orange. It may be synthesized from isoprene or acetylene in several steps. Natural citral is a mixture of cis and trans isomers (Z and E isomers by newer nomenclature) also known as neral and geranial. Either isomer or a mixture of both in any proportion may be used in the process of the invention; likewise either the natural or synthetic citral may be employed.

The ketones of the formula (II) given above are also well known as are methods of their preparation. Preferred ketones of formula (II) are those wherein $R_1$ and $R_2$ are independently selected from the group consisting of branched or linear, saturated or unsaturated, aliphatic or cycloaliphatic hydrocarbyl of from 1 to 20 carbon atoms, inclusive (most preferably 1 to 16 carbon atoms).

Representative of preferred ketones of the formula (II) are: acetone, methyl ethyl ketone, methyl n-propyl ketone, methyl isopropyl ketone, methyl n-butyl ketone, methyl isobutyl ketone, methyl tert-butyl ketone, diethyl ketone, diacetyl, 2-methyl-2-hepten-6-one, acetophenone, cyclohexanone, cyclohexyl ethyl ketone, benzyl methyl ketone, methyl propenyl ketone, ethyl propenyl ketone, mesityl oxide, propyl propenyl ketone, isobutylideneacetone, 2-methyl-2,4-heptadien-6-one, β-ionone, farnesylacetone and geranylacetone.

The process of the invention may be carried out under anhydrous conditions or in the presence of water, preferably under substantially anhydrous conditions.

The catalyst, lithium hydroxide, employed in the method of the invention is a well known compound, commercially available. The catalyst may be employed in its anhydrous or its hydrated forms.

Lithium hydroxide monohydrate is a catalyst most preferred because of an associated higher yield which may result from its very low solubility in the reaction mixture. The catalyst is employed in a catalytic proportion. The optimal proportion of catalyst to be employed is variable over a wide range, and may be determined by the desired reaction rate, reactor design, whether the reaction is to be carried out batchwise or continuously, and other such factors well known to those skilled in the art of catalytic reaction processes.

In general, the catalytic proportion may be down to the 0.01 % level in the event relatively pure starting materials are employed based on the weight of citral reactant. The rate of the reaction appears to be independent of the amount of solid catalyst down to the proportion which serves to saturate the reaction mixture; in other words, the rate appears to depend on the dissolved catalyst and is not a heterogeneous reaction on the surface of the catalyst. Accordingly, an upper limit on the proportion of catalyst used may be that which will dissolve to saturate the reaction mixture. However, the maximum amount of catalyst within the meaning of a "catalytic proportion" is only governed by practical circumstances and may be several times the weight of the reactants present in the reaction mixture at a given time. Since the reaction involves a substantially solid catalyst, adequate stirring or other means for attaining fluid movement should be provided to keep the catalyst in good contact with the reactants so that there is enough dissolved catalyst to attain a rapid rate of reaction. When the reactor vessel is a column packed with catalyst, the desired contact with a maximum proportion of catalyst is achieved by movement of the reactants through the column.

The mode of carrying out the process of the invention may be either batchwise or continuous. In the batchwise mode, the catalyst is stirred with the liquid reactants and at the end of the reaction it may be filtered out and the remaining solution separated to obtain the desired product, employing conventional techniques. It is economically advantageous to distill off the unreacted excess ketone (II) for recycle. To render the product pseudoionone more stable to distillation, it is preferred to remove the catalyst and to neutralize any that remains dissolved by addition of a weak acid such as carbon dioxide. Lithium hydroxide is particularly well adapted to removal at the end of the reaction by filtration, since it has very limited solubility in the reaction product mixture.

The process of the invention may be carried out at a temperature of from about $-20°$ C. to about $240°$ C. although the range of $-10°$ C. to $150°$ C. is preferred. At the higher reaction temperatures the reaction times will be shorter. Progress of the condensation may be followed by conventional analytical technique, such as by gas chromatograph analysis. The reaction period of the reaction is from 5 minutes to 100 hours or more, preferably from 30 minutes to 10 hours, depending on the reaction temperature and the reactivity of the starting compounds.

The process may be carried out at atmospheric or superatmospheric pressure, for example at pressures of from 1 to 100 atmospheres. The pressure and temperature are chosen so that the reaction mixture is liquid.

The process may be carried out in the absence of solvents or in the presence of a solvent which is inert. The term "inert solvent" means a solvent for a reactant which does not enter into or adversely affect the desired course of the condensation. Of course, the stoichiometric excess of ketone preferably used in the method of the invention may also function as a solvent for particular aldehydes. Representative of other inert solvents are: dialkyl ethers such as di-n-butyl ether, aliphatic hydrocarbons such as ligroin, or aromatic hydrocarbons such as toluene or xylene. The solvent may be used in an amount which is about twice to five times by weight the sum of the weights of the starting components.

Since some of the product compounds formed by the method of the invention may be sensitive to air it has proved to be advantageous to carry out the reaction while excluding air, for example under an atmosphere of nitrogen or argon.

Advantageously, the reaction mixture will be held at the reaction conditions until 90% or more of the citral has reacted.

In the continuous mode of carrying out the process of the invention, the catalyst may be placed in a column or other vessel through which the mixed reactants are passed at such a rate and for such a time that, preferably, over about 90% of the citral reacts. Then the effluent solution may be passed, optionally by way of a crude product storage vessel, to a recovery still wherein the excess ketone is stripped off for possible recycle. The residual product is then preferably freed of dissolved catalyst by treatment with weak acid such as carbon dioxide, filtered free of any remaining solids, and then distilled to isolate the product.

The following examples describe the manner and process of the invention and set forth the best mode contemplated by the inventor for carrying out the invention but are not to be construed as limiting.

EXAMPLE 1

A mixture of 2.0 g citral (95%, 12.5 mmol), 15.0 g acetone (259 mmol) and 4.0 g lithium hydroxide monohydrate (95 mmol., 7.6 equiv.) was refluxed with stirring and samples taken for analysis at various times. The results are given in Table 1, below:

TABLE 1

| Component | GC AREA % RESULTS Reaction Time (min) | | | | | Final Product Oil |
|---|---|---|---|---|---|---|
| | 30 | 98 | 148 | 198 | 273 | |
| Diacetone alc. | 13.2 | 11.0 | 9.4 | 9.6 | 12.4 | 9.0 |
| Neral | 15.4 | 7.2 | 3.4 | 2.3 | — | — |
| Geranial | 25.1 | 10.2 | 4.6 | 3.1 | 1.4 | 1.3 |
| Pseudoionone | 27.4 | 45.4 | 54.0 | 51.8 | 53.2 | 54.5 |

The mixture was filtered, the solids washed with acetone, and combined filtrates treated with carbon dioxide and then evaporated under vacuum. The residual yellow oil weighed 2.76 g and was found by GC analysis to contain 77.8 wt % pseudoionone, corresponding to a yield of 89.5 mole %.

Reduction of the amount of lithium hydroxide monohydrate to as low as 0.19 equivalents gave a comparably high pseudoionone yield, 87.0%. This indicates that the reaction is catalyzed by dissolved lithium hydroxide and the amount required is just enough to saturate the solution at reflux temperature.

EXAMPLE 2

This example demonstrates the improvement obtained by using lithium hydroxide over the prior art aqueous sodium hydroxide.

Reaction A — lithium hydroxide:

A mixture of 4.0 g. citral (95%, 25 mmol), 15.2 g acetone (262 mmol, 10.5 equiv.) and 4.0 g lithium hydroxide monohydrate (95 mmol, 3.8 equiv.) was heated to reflux for 4 hrs. The crude oil, 5.7 g, contained 74.1 wt. % pseudoionone, corresponding to a yield of 87.7 mole %.

Reaction B — aqueous sodium hydroxide:

A mixture of 2.0 g. citral (95%, 12.5 mmol), 7.6 g acetone (132 mmol, 10.5 equiv.), 0.6 g 10% sodium hydroxide (1.6 mmol, 0.12 equiv.), and 1.4 g water was stirred at room temperature for 19 hours. The crude oil, 2.9 g, contained 64.7 wt % pseudoionone corresponding to a yield of 76.7 mole %.

EXAMPLE 3

500 g citral (75%) and 2008 g acetone were heated at reflux (50° – 60° C.) in the presence of 5 g lithium hydroxide monohydrate until 1% citral remained. The crude oil was neutralized with 8% aqueous phosphoric acid, stripped of acetone, and washed with water and aqueous sodium bicarbonate to give ann 85% molar yield of pseudoionone. The product contained 1% of isocitral aldol impurities as compared with 3% isocitral aldols in the prior art sodium hydroxide process.

EXAMPLE 4

A mixture of 7.6 g citral (95%, 47.5 mmol), 18.0 g methyl ethyl ketone (250 mmol, 5.3 equiv.), 0.2 g lithium hydroxide monohydrate (4.8 mmol, 0.1 equiv.) and 1.0 g $C_{13}$ internal standard was refluxed with stirring for 5 hours. With a citral conversion of 97.5%, the yield of methylpseudoionone was 85 mole %. The relative isomer ratio was as follows:

| Isomer | Relative Percent |
|---|---|
| iso-methyl, beta-trans, cis | 3.8 |
| n-methyl, beta-trans, cis | 33.4 |
| iso-methyl, beta-trans, trans | 5.0 |
| n-methyl, beta-trans, trans | 57.8 |

What is claimed is:

1. A method of preparing a pseudoionone which comprises: condensing citral with a ketone in the presence of a catalytic proportion of lithium hydroxide.

2. A method of preparing a pseudoionone of the formula:

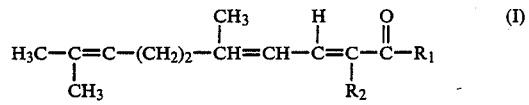

wherein $R_1$ represents hydrocarbyl of from 1 to 25 carbon atoms, inclusive; $R_2$ independently is selected from the group consisting of hydrogen and aliphatic hydrocarbyl of 1 to 10 carbon atoms, inclusive: and $R_1$ and $R_2$ when taken together with the two adjacent carbon atoms to which they are attached are members of an alicyclic ring, which comprises; the condensation of citral with a ketone of the formula:

wherein $R_1$ and $R_2$ have the meanings previously ascribed to them; in the presence of a catalytic proportion of lithium hydroxide.

3. The method of claim 2 where the ketone is acetone.

4. The method of claim 2 where the catalyst is lithium hydroxide monohydrate.

5. The method of claim 2 where the reaction mixture is passed through a column packed with the catalyst.

6. The method of claim 2 where the process is carried out continuously.

7. The method of claim 2 where the product mixture is filtered to remove solid lithium hydroxide and then treated with carbon dioxide to convert dissolved lithium hydroxide to lithium carbonate.

8. The method of claim 2 wherein the reaction mixture is saturated with lithium hydroxide monohydrate.

9. The method of claim 2 wherein the mixture of citral and acetone is circulated through a column packed with lithium hydroxide monohydrate.

10. The method of claim 2 wherein the ketone is methylethylketone.

11. The method of claim 2 carried out under substantially anhydrous conditions.

12. The method of claim 1 wherein the reaction is conducted in the absence of a solvent.

13. The method of claim 2 wherein the reaction is conducted in the absence of a solvent.

14. The method of claim 3 wherein the reaction is conducted in the absence of a solvent.

15. The method of claim 4 wherein the reaction is conducted in the absence of a solvent.

* * * * *